United States Patent [19]

Suto et al.

[11] Patent Number: 5,420,109

[45] Date of Patent: May 30, 1995

[54] CYTOKINE RESTRAINING AGENTS

[75] Inventors: Mark J. Suto; Beverly E. Girten, both of San Diego; Richard A. Houghten, Solana Beach; Costas C. Loullis, Cardiff; Ronald R. Tuttle, Escondido, all of Calif.

[73] Assignee: Houghten Pharmaceuticals, Inc., San Diego, Calif.

[21] Appl. No.: 151,534

[22] Filed: Nov. 12, 1993

[51] Int. Cl.$^6$ ............... A61K 38/00; C07K 5/00; C07K 7/00; C07K 17/00

[52] U.S. Cl. ......................... 514/8; 514/16; 514/17; 514/18; 530/317; 530/322; 530/328; 530/329; 530/330

[58] Field of Search ................. 514/16–18, 514/8; 530/317, 322, 328, 329, 330

[56] References Cited

U.S. PATENT DOCUMENTS

| | | | |
|---|---|---|---|
| 4,457,864 | 7/1984 | Hruby et al. | 260/112.5 |
| 4,485,039 | 11/1984 | Hruby et al. | 260/112.5 R |
| 4,649,191 | 3/1987 | Hruby | 530/329 |
| 4,866,038 | 9/1989 | Hruby et al. | 514/14 |
| 4,918,055 | 4/1990 | Hruby et al. | 514/14 |
| 5,028,592 | 7/1991 | Lipton | 514/18 |
| 5,049,547 | 9/1991 | Hruby et al. | 54/14 |
| 5,157,023 | 10/1992 | Lipton | 514/18 |

FOREIGN PATENT DOCUMENTS

| | | |
|---|---|---|
| 292291 | 5/1988 | European Pat. Off. . |
| 427458 | 5/1991 | European Pat. Off. ...... A61K 37/02 |
| 568925 | 4/1993 | European Pat. Off. . |
| WO87/04623 | 8/1987 | WIPO . |

OTHER PUBLICATIONS

Dinarello, Charles A. and Wolff, Sheldon, M. "The Role of Interleukin-1 in Disease." New England J. Med. 328:106–113 (1993).

Richard, D. B. and Lipton, J. M. "Effect of α-MSH 11-13 (Lysine-Proline-Valine) on Fever in the Rabbit." Peptides 5:815–817 (1984).

Deeter, L. B. et al. "Antipyretic Properties of Centrally Administered α-MSH Fragments in the Rabbit." Peptides 9:1285–1288 (1989).

Sugg, Elizabeth E. et al. "D-Isomeric Replacements Within the 6-9 Core Sequence of a Ac-[Nle$^4$]-α-MSH-4-11-NH$_2$: A Topological Model for the Solution Conformation of a α-Melanotropin." Biopolymers 25:2029–2042 (1986).

Norlund, James J. "α-Melanocyte-Stimulating Hormone A Ubiquitous Cytokine with Pigmenting Effects." JAMA 266:2753–2754 (1991).

Levine, Norman et al. "Induction of Skin Tanning by Subcutaneous Administration of a Potent Synthetic Melanotropin." JAMA 266:2730–2736 (1991).

Al-Obeidi, Fahad et al. "Design of a New Class of Superpotent Cyclic α-Melanotrophins Based on Quenched Dynamic Simulations." J. Am. Chem. Soc. 111:3413–3416 (1989).

Poole, S. et al. "Peripheral Analgesic Activities of Peptides Related to α-Melanocyte Stimulating Hormone and Interleukin-1$\beta^{193-195}$." Br. J. Pharmacol. 106:489–492 (1992).

*Primary Examiner*—Jill Warden
*Assistant Examiner*—Sheera J. Muff
*Attorney, Agent, or Firm*—Campbell and Flores

[57] ABSTRACT

The present invention provides novel cytokine restraining agents, which limit or control the biological activity of cytokines. The invention also provides pharmaceutical compositions comprising a cytokine restraining peptide and methods of administering the pharmaceutical composition to a subject. The invention further provides methods for using the novel peptides to restrain cytokine activity in a subject.

24 Claims, No Drawings

CYTOKINE RESTRAINING AGENTS

BACKGROUND OF THE INVENTION

1. Field of the Invention

This invention relates generally to the fields of peptide chemistry and molecular pathology and, more specifically, to novel cytokine restraining agents.

2. Background Information

Cytokines are a class of proteins produced by macrophages and monocytes in response to viral or bacterial infection and in response to T cell stimulation during an immune response. Cytokines are normally present in very low concentrations in a tissue and mediate their effects through binding to high affinity receptors on specific cell types.

Various cytokines such as the interleukins (IL), interferons (IF) and tumor necrosis factor (TNF) are produced during immune and inflammatory responses and control various aspects of these responses. Following induction of an immune or inflammatory response, the concentrations of the various cytokines increase at different times. For example, following exposure of a subject to bacterial endotoxin, TNF and interleukin-6 (IL-6) levels increase, followed a few hours later by increases in the levels of IL-1 and IL-8

TNF, IL-1, IL-6 and IL-8 mediate host defense responses, cell regulation and cell differentiation. For example, these cytokines can induce fever in a subject, cause activation of T and B cells and affect the levels of other cytokines, which result in a cascade effect whereby other cytokines mediate the biological action of the first cytokine.

The activation of these four cytokines is responsible for the tissue damage and pain that occurs in various inflammatory conditions including, for example, rheumatoid arthritis. In rheumatoid arthritis, levels of TNF, IL-1, IL-6 and IL-8 increase dramatically and can be detected in the synovial fluid. The cytokine cascade induced by expression of these cytokines results in depressed lipoprotein metabolism as well as bone and cartilage destruction. In bacterial infections, cytokines such as IL-8 act as a signal that attracts white blood cells such as neutrophils to the region of cytokine expression. In general, the release of enzymes and superoxide anions by neutrophils is essential for destroying the infecting bacteria. However, if cytokine expression causes neutrophils to invade, for example, the lungs, release of neutrophil enzymes and superoxide anion can result in the development of adult respiratory distress syndrome, which can be lethal. Similarly, neutrophil invasion in response to cytokine expression in other tissues and organs can lead to destruction of healthy tissue.

Cytokines have multiple biological activities and interact with more than one cell type. In addition, some cells interact with more than one type of cytokine. As a result, it has not been possible to prevent damage to healthy tissue by targeting one particular cytokine or cell type. For example, individual cytokine receptors or receptor antagonists that were designed to eliminate the biological effect due to one cytokine did not decrease mortality due to endotoxic shock, which is mediated by TNF, IL-1, IL-6 and IL-8.

A better approach for preventing tissue damage due to cytokines would be to restrain the expression of all or several of the cytokines involved in the response, without eliminating expression of any cytokine in its entirety. In this way, complete immunosuppression can be prevented and homeostasis can be maintained. Corticosteroids effectively modulate cytokine expression. However, corticosteroids can cause complete immunosuppression and have other undesirable side effects such as inducing "wasting" syndrome, diabetes and osteoporosis. Non-steroidal anti-inflammatory drugs such as ketorolac (Toradol®; Syntex) also are effective in treating inflammation and pain. However, these drugs act by inhibiting prostaglandin production, which can lead to potentially severe complications including gastric ulceration, bleeding and renal failure.

In order to prevent pathological conditions caused by the expression of cytokines, it would be advantageous if cytokine levels could be readily controlled in a tissue. However, modifying the physiologic effect of cytokines has been hindered due to their pleiotropic effects. Thus, a need exists for agents that can restrain the activity of cytokines in a subject without causing undesirable side effects. The present invention satisfies this need and provides related advantages as well.

SUMMARY OF THE INVENTION

The present invention relates to novel peptides that are potent cytokine restraining agents. Novel cytokine restraining peptides having the general structures, $X_1$ - $X_2$ - His - (D)Phe - Arg - (D)Trp - $X_3$ and $X_4$ - His - (D)Phe - Arg - (D)Trp - $X_3$, where $X_1$, $X_2$, $X_3$ and $X_4$ can be amino acids or amino acid analogs, are disclosed. The invention also relates to pharmaceutical compositions comprising a pharmaceutically acceptable carrier and a cytokine restraining agent and to methods of administering the pharmaceutical composition to a subject. Administration of such a cytokine restraining agent to a subject restrains, but does not completely suppress, cytokine activity. Thus, the present invention provides a method for preventing or minimizing damage to healthy tissue caused by cytokine activity in a subject without causing complete immunosuppression in the subject.

DETAILED DESCRIPTION OF THE INVENTION

The present invention generally relates to novel cytokine restraining agents having the structure: $X_1$ - $X_2$ - His - (D) PHE - Arg - (D)Trp - $X_3$, wherein $X_1$ is

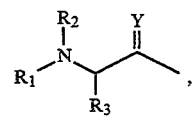

H or $COCH_3$;

$X_2$ is

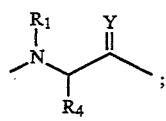

and $X_3$ is

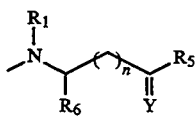

or NH$_2$;

wherein Y is O, H$_2$ or S; R$_1$ is H, COCH$_3$, C$_2$H$_5$, CH$_2$Ph, COPh, COO-t-butyl, COOCH$_2$Ph, CH$_2$CO-(polyethylene glycol) or A; R$_2$ is H or COCH$_3$; R$_3$ is a linear or branched alkyl group having 1 to 6 carbon atoms; R$_4$ is (CH$_2$)$_m$-CONH$_2$, (CH$_2$)$_m$-CONHR$_1$ or (CH$_2$)$_m$-CONHA; R$_5$ is OH, OR$_3$, NH$_2$, SH, NHCH$_3$, NHCH$_2$Ph or A; and R$_6$ is H or R$_3$;

and wherein "Ph" is C$_6$H$_5$, "m" is 1, 2 or 3, "n" is 0, 1, 2 or 3, and "A" is a carbohydrate having the general formula

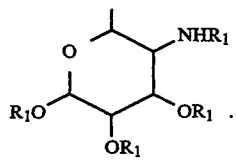

The present invention also relates to novel cytokine restraining agents having the structure: X$_4$ - His - (D)Phe - Arg - (D) Trp - X$_3$, wherein
X$_4$ is

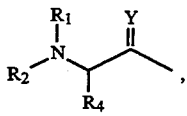

H or COCH$_3$;
X$_3$ is

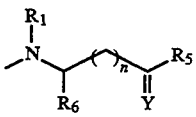

or NH$_2$;

wherein Y is O, H$_2$ or S; R$_1$ is H, COCH$_3$, C$_2$H$_5$, CH$_2$Ph, COPh, COO-t-butyl, COOCH$_2$Ph, CH$_2$CO-(polyethylene glycol) or A; R$_2$ is H or COCH$_3$; R$_4$ is (CH$_2$)$_m$-CONH$_2$, (CH$_2$)$_m$-CONHR$_1$ or (CH$_2$)$_m$-CONHA; R$_5$ is OH, OR$_3$, NH$_2$, SH, NHCH$_3$, NHCH$_2$Ph or A; and R$_6$ is H or R$_3$;

and wherein "Ph" is C$_6$H$_5$, "m" is 1, 2 or 3, "n" is 0, 1, 2 or 3, and "A" is a carbohydrate having the general formula

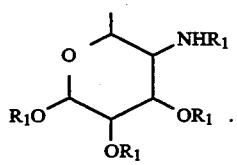

As used herein, the term "restrain" has its commonly understood meaning, i.e., to limit, restrict, keep under control or moderate. It follows that a "cytokine restraining agent" is an agent that has an action that limits or controls the biological activity of a cytokine. A cytokine restraining agent can be, for example, a peptide comprising amino acids or amino acid analogs as described herein. Representative examples of peptide cytokine restraining agents include:

1) Nle -Gln - His - (D)Phe - Arg - (D)Trp - Gly-NH$_2$;
2) Ac-Nle -Gln - His - (D)Phe - Arg - (D)Trp - Gly-NH$_2$;
3) Ac-Nle -Gln - His - (D)Phe - Arg - (D)Trp - Gly-OH;
4) Ac-Nle -Gln - His - (D)Phe - Arg - (D)Trp - Gly-OC$_2$H$_5$;
5) Ac-Nle -Gln - His - (D)Phe - Arg - (D)Trp - Gly-NH-NH$_2$;
6) Ac-Nle -Asn - His - (D)Phe - Arg - (D)Trp - Gly-NH$_2$;
7) Ac-Nle -Asn - His - (D)Phe - Arg - (D)Trp - Gly-OH;
8) Ac-Nle -Gln - His - (D)Phe - Arg - (D)Trp - Gly-NHCH$_2$CH$_2$Ph;
9) Ac-Nle -Gln - His - (D)Phe - Arg - (D)Trp - Gly-NHCH$_2$Ph; and 10) 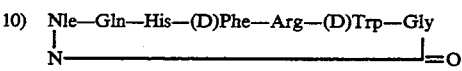

11) Ac-Gln - His - (D)Phe - Arg - (D)Trp - Gly-NH$_2$
12) Ac-Nle -Gln - His - (D)Phe - Arg - (D)Trp-NH$_2$
13) Ac-His - (D)Phe - Arg - (D)Trp-NH$_2$

Peptide cytokine restraining agents as described above are characterized, in part, by a core structure having the amino acid sequence, His - (D)Phe - Arg - (D)Trp, where the amino acids are indicated by their commonly known three letter code and where (D) designates an amino acid having the "D" configuration, as opposed to the naturally occurring L-amino acids. Where no specific configuration is indicated, one skilled in the art would understand the amino acid to be an (L)-amino acid. In the peptides exemplified above, "Nle" is the three letter code for norleucine and "Ph" indicates a "phenyl" group (C$_6$H$_5$).

Cytokine restraining agents such as the peptides described above were synthesized using a modification of the solid phase peptide synthesis method of Merrifield (J. Am. Chem. Soc., 85:2149 (1964), which is incorporated herein by reference) or can be synthesized using standard solution methods well known in the art (see, for example, Bodanszky, M., Principles of Peptide Synthesis (Springer-Verlag, 1984), which is incorporated herein by reference). Peptides prepared by the method of Merrifield can be synthesized using an automated peptide synthesizer such as the Applied Biosystems 431A-01 Peptide Synthesizer (Mountain View, Calif.) or using the manual peptide synthesis technique described by Houghten, Proc. Natl. Acad. Sci., USA 82:5131 (1985), which is incorporated herein by reference.

Peptides were synthesized using amino acids or amino acid analogs, the active groups of which were protected as required using, for example, a t-butyldicarbonate (t-BOC) group or a fluorenylmethoxy carbonyl (FMOC) group. Amino acids and amino acid analogs can be purchased commercially (Sigma Chemical Co.; Advanced Chemtec) or synthesized using methods known in the art. Peptides synthesized using the solid phase method can be attached to resins including 4- methylbenzhydrylamine (MBHA), 4-(oxymethyl)-phenylacetamido methyl and 4-(hydroxymethyl)-phenoxymethyl-copoly(styrene-1% divinylbenzene) (Wang resin), all of which are commercially available, or to p-nitrobenzophenone oxime polymer (oxime resin), which can be synthesized as described by De Grado and Kaiser, *J. Org. Chem.* 47:3258 (1982), which is incorporated herein by reference.

One skilled in the art would know that the choice of amino acids or amino acid analogs incorporated into the peptide will depend, in part, on the specific physical, chemical or biological characteristics required of the cytokine restraining peptide. Such characteristics are determined, in part, by the route by which the cytokine restraining agent will be administered or the location in a subject to which the cytokine restraining agent will be directed.

Selective modification of the reactive groups in a peptide also can impart desirable characteristics to a cytokine restraining agent. Peptides can be manipulated while still attached to the resin to obtain N-terminal modified compounds such as an acetylated peptide or can be removed from the resin using hydrogen fluoride or an equivalent cleaving reagent and then modified. Compounds synthesized containing the C-terminal carboxy group (Wang resin) can be modified after cleavage from the resin or, in some cases, prior to solution phase synthesis. Methods for modifying the N-terminus or C-terminus of a peptide are well known in the art and include, for example, methods for acetylation of the N-terminus or methods for amidation of the C-terminus. Similarly, methods for modifying side chains of the amino acids or amino acid analogs are well known to those skilled in the art of peptide synthesis. The choice of modifications made to the reactive groups present on the peptide will be determined by the characteristics that the skilled artisan requires in the peptide.

A cyclic peptide also can be an effective cytokine restraining agent. A cyclic peptide can be obtained by inducing the formation of covalent bond between, for example, the amino group at the N-terminus of the peptide and the carboxyl group at the C-terminus. Alternatively, a cyclic peptide can be obtained by forming a covalent bond between a terminal reactive group and a reactive amino acid side chain or between two reactive amino acid side chains. One skilled in the art would know that the choice of a particular cyclic peptide is determined by the reactive groups present on the peptide as well as the desired characteristic of the peptide. For example, a cyclic peptide may provide a cytokine restraining agent with increased stability in vivo.

A newly synthesized peptide can be purified using a method such as reverse phase high performance liquid chromatography (RP-HPLC), which is described in detail below (see Example I), or other methods of separation based on the size or charge of the peptide. Furthermore, the purified peptide can be characterized using these and other well known methods such as amino acid analysis and mass spectrometry, which is described in detail below (see Example I).

The invention also relates to pharmaceutical compositions comprising a cytokine restraining agent and a pharmaceutically acceptable carrier. Pharmaceutically acceptable carriers are well known in the art and include aqueous solutions such as physiologically buffered saline or other solvents or vehicles such as glycols, glycerol, oils such as olive oil or injectable organic esters.

A pharmaceutically acceptable carrier can contain physiologically acceptable compounds that act, for example, to stabilize the cytokine restraining agent or increase the absorption of the agent. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the cytokine restraining agent and on the particular physico-chemical characteristics of the specific cytokine restraining agent.

The invention further relates to methods of administering a pharmaceutical composition comprising a cytokine restraining agent to a subject in order to restrain pathologically elevated cytokine activity in the subject. For example, the composition can be administered to a subject as a treatment for inflammation, pain, cachexia and patho-immunogenic diseases such as arthritis, inflammatory bowel disease and systemic lupus erythematosus, each of which is characterized by pathologically elevated cytokine activity. As used herein, the term "pathologically elevated" means that a cytokine activity is elevated above a range of activities which is expected in a normal population of such subjects. For example, a normal range of IL-1 activity present in a specific tissue can be determined by sampling a number of subjects in the population. A subject having a pathology characterized by cytokine-induced pathological effects can be readily identified by determining that the cytokine activity in the subject is pathologically elevated, which is above the normal range.

One skilled in the art would know that a pharmaceutical composition comprising a cytokine restraining agent can be administered to a subject having pathologically elevated cytokine activity by various routes including, for example, orally, intravaginally, rectally, or parenterally, such as intravenously, intramuscularly, subcutaneously, intraorbitally, intracapsularly, intraperitoneally, intracisternally or by passive or facilitated absorption through the skin using, for example, a skin patch or transdermal iontophoresis, respectively. Furthermore, the composition can be administered by injection, intubation or topically, the latter of which can be passive, for example, by direct application of an ointment or powder, or active, for example, using a nasal spray or inhalant. A cytokine restraining agent also can be administered as a topical spray, in which case one component of the composition is an appropriate propellant. The pharmaceutical composition also can be incorporated, if desired, into liposomes, microspheres or other polymer matrices (Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively simple to make and administer.

As described previously, cytokine expression can result in damage to healthy tissue in a subject and, in extreme cases, can lead to severe disability and death. Cytokines can be expressed at a site of localized infection or can be expressed systemically, for example, in an immune response or in response to bacterial endotoxin-induced sepsis. Cytokine expression can induce pyrexia (fever) and hyperalgesia (extreme sensitivity to pain) in a subject, as well as macrophage and monocyte activation, which produces or further contributes to an inflammatory response in a subject.

Since cytokine expression can be localized or systemic, one skilled in the art would select a particular route and method of administration of the cytokine restraining agent based on the source and distribution of cytokines in a subject. For example, in a subject suffering from a systemic condition such as bacterial endotoxin-induced sepsis, a pharmaceutical composition comprising a cytokine restraining agent can be administered intravenously, orally or by another method that distributes the cytokine restraining agent systemically. However, in a subject suffering from a pathology caused by localized cytokine expression such as acute respiratory distress syndrome, a cytokine restraining agent can be suspended or dissolved in the appropriate pharmaceutically acceptable carrier and administered directly into the lungs using a nasal spray.

In order to restrain the biological activity of a cytokine, the cytokine restraining agent must be administered in an effective dose, which is about 0.01 to 100 mg/kg body weight. The total effective dose can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of a cytokine restraining agent required to obtain an effective dose in a subject depends on many factors including the age and general health of the subject as well as the route of administration and the number of treatments to be administered. In view of these factors, the skilled artisan would adjust the particular dose so as to obtain an effective dose for restraining cytokine activity.

Examples of cytokine restraining agents and the effectiveness of a cytokine restraining agent in preventing or minimizing adverse biological effects mediated by cytokines are provided below and summarized in Table I. As described below, a cytokine restraining agent such as the peptide shown in Example II effectively restrains cytokine expression in mice (Examples III and IV) and provides relief from cytokine-mediated pain, swelling, fever and lethality in mice and rats using mouse and rat model systems that are recognized in the art as potential predictors of efficacy in humans (Examples V to IX). Thus, the compounds described herein can be used as medicaments for the treatment of pathologies such as inflammation, pain, cachexia and patho-immunogenic diseases such as arthritis, inflammatory bowel disease and systemic lupus erythematosus, which are characterized by altered cytokine activity.

The following examples are intended to illustrate but not limit the invention.

EXAMPLE I

Synthesis of a Peptide Cytokine Restraining Agent Having the Sequence

Nle -Gln - His - (D) Phe - Arg - (D)Trp - Gly-NH$_2$

This example describes a method for solid phase synthesis of a peptide cytokine restraining agent.

A peptide cytokine restraining agent having the amino acid sequence, Nle -Gln - His - (D)Phe - Arg - (D)Trp -.Gly, was synthesized using a modification of the solid phase peptide synthesis method of Merrifield (1964). Essentially, MBHA resin containing a t-BOC glycine derivative (Advanced Chemtech; Louisville, Ky.) was added to a reaction vessel suitable for solid phase peptide synthesis (see Houghten, 1985). The resin was washed three times with methylene chloride and the t-BOC protecting group was removed using trifluoroacetic acid (TFA) containing 1–2% anisole in methylene chloride. The resin then was washed with methylene chloride and treated with diisopropylethylamine.

The peptide was extended by the addition of 3.2 equivalents of N-formyl-BOC-protected D-tryptophan in dimethylformamide and 3.0 equivalents of dicyclohexylcarbodiimide. The reaction was monitored using ninhydrin and was allowed to proceed for 25 min, after which the resin was washed using methylene chloride. The procedure was repeated using di-tolulyl-BOC arginine, then with each of the desired protected amino acids until the complete heptapeptide was synthesized.

Following synthesis of the heptapeptide, the N-formyl protecting group on the tryptophan residue was removed using 20% piperidine in DMF and the resin was washed with methylene chloride. The peptide was cleaved from the resin using anhydrous hydrogen fluoride (HF) containing 10% anisole, the reaction mixture was concentrated and the residue was digested with aqueous acetic acid. The acetic acid fraction, which contained the digested sample, was removed and the residue was washed with water. The wash was added to the acetic acid fraction and the combined sample was concentrated. The resulting crude peptide was purified by RP-HPLC (Vydac, C-18 column, using a gradient of 1 to 60% solution B over 30 min (solution A is 0.1% TFA/water and solution B is 0.1% TFA/acetonitrile).

The peptide was determined to be 97% pure by RP-HPLC (Vydac C-18 column, using isocratic 24% solution B; solution A and solution B, as above; absorption determined at 215 nm). The mass of the purified heptapeptide was determined by plasma absorption mass spectrometry using a Biolon 20 Mass Analyzer time of flight detector. The mass of the peptide was measured to be 942.7, which was essentially the same as the expected molecular mass (MS (M+1)=942.2).

EXAMPLE II

Preparation of a Peptide Cytokine Restraining Agent Having the Sequence

Ac-Nle -Gln - His - (D)Phe - Arg - (D)Trp - Gly-NH$_2$

This example describes a method for preparing an N-acetylated peptide cytokine restraining agent.

The heptapeptide was synthesized as described in Example I, except that prior to cleaving the newly synthesized peptide from the resin, the amino terminus of the peptide was acetylated by treating the sample with acetic anhydride, diisopropylethylamine and methylene chloride for 2 hr. Following acetylation, the heptapeptide was cleaved from the resin, purified by RP-HPLC and characterized by mass spectrometry, as described above. The acetylated heptapeptide of Example II, designated, here, as EX-2, was determined to be 98% pure and the mass was measured to be 985.2 daltons, which was same as the expected molecular mass.

EXAMPLE III

Reduction of Lipopolysaccharide-Induced Tumor Necrosis Factor Levels in Mice This example describes the effectiveness of a cytokine restraining agent for decreasing tumor necrosis factor (TNF) levels in lipopolysaccharide (LPS; endotoxin) treated mice.

Balb/c female mice weighing approximately 20 g were placed into two groups, a control group and a treated group. Five mg/kg of LPS in 0.9% saline was administered by intraperitoneal (ip) injection into the control mice. Mice in the treated group were first injected ip with 30 µg of EX-2 in saline, then, one minute after EX-2 was administered, the mice received LPS as described for the control group.

Blood samples were collected from the orbital sinus of treated and control mice at various times up to four hours after LPS was administered. The plasma was separated by centrifugation at 3000×g for 5 min, then diluted with four volumes of 1 x phosphate buffer saline (pH 7.4) containing 1% bovine serum albumin. A 100 µl sample of serum was assayed by ELISA for TNF-α (Genzyme; Cambridge Mass.).

The mean (±SEM) TNF-α level in six mice from each group was determined and the percent reduction in TNF levels was calculated. As shown in Table I, treatment of mice with EX-2 resulted in a 50% decrease in the level of TNF-α as compared to untreated control mice.

EXAMPLE IV

Reduction of Lipopolysaccharide-Induced Interleukin-6 Levels in Mice

This example describes the effectiveness of a cytokine restraining agent for decreasing interleukin-6 (IL-6) levels in LPS treated mice.

Balb/c mice were grouped and treated as described in Example III, above. Blood samples were obtained from the orbital sinus at various times up to six hours and serum was collected and diluted as described above. A 100 µl aliquot was assayed for IL-6 levels using an IL-6-specific ELISA by a modification of the method of Starnes et al., *J. Immunol.* 145:4185–4194 (1990), which is incorporated herein by reference.

The mean (±SEM) IL-6 level in six mice from each group was determined and the percent reduction in IL-6 was calculated. As shown in Table I, treatment of mice with EX-2 resulted in a 60% decrease in the level of IL-6 as compared to untreated control mice.

TABLE I

BIOLOGICAL DATA FOR CYTOKINE RESTRAINING AGENTS

| Biological Test | Dose | Efficacy |
| --- | --- | --- |
| Reduction in TNF levels | 30 µg/mouse | 50% |
| Reduction in IL-6 levels | 300 µg/mouse | 60% |
| Reduction in Carageenan-induced Paw Swelling | 1 µg/mouse | 45% |
| Inhibition of LPS-induced Lethality | 11 × 300 µg/mouse | 83% |
| Reduction in IL-1-induced Hyperalgesia | 1 µg/mouse | 125% |
| Reduction in LPS-induced PMN Count | 100 µg/kg | 58% |
| Reduction in IL-1-induced Fever | 500 µg/kg | 52% |
| Reduction in LPS-induced Fever | 50 µg/kg | 45% |

EXAMPLE V

Carageenan-Induced Paw Swelling

This example describes the effectiveness of a cytokine restraining agent for alleviating inflammation and pain.

Carageenan-induced paw swelling was induced using a modification of the methods of Hiltz and Lipton, *Peptides* 11:979–982 (1990); Vinegar et al., *Fed. Proc.* 46:118–126 (1987); and Vinegar et al., *J. Pharmacol. Expt. Therap.* 166:96–103 (1969), each of which is incorporated herein by reference. Briefly, adult female Balb/c mice were anesthetized by ip injection of 7 mg/kg ketamine and 0.6 mg/kg rompun. Foot pad thickness was measured using a spring loaded micrometer (Swiss Precision Instruments). Foot pad thickness was expressed in units of 1/100 inch. After baseline measurements were obtained, mice were injected into a hind foot pad with either 0.2 ml physiologic saline (control) or varying doses of EX-2 in 0.2 ml saline (treated). The first injection was followed immediately by injection of 0.02 ml of 0.15% κ-carageenan (Sigma Chemical Co.).

Hind foot pad thickness was measured hourly for six hours, the change in thickness was determined and the percent reduction in swelling due to treatment with EX-2 was calculated. As shown in Table I, ip injection of 1 µg EX-2 reduced carageenan-induced swelling by 45% when measured at the 2 hr time point.

EXAMPLE VI

Lipopolysaccharide-Induced Lethality

This example describes the effectiveness of a cytokine restraining agent, EX-2, in reducing lethality from sepsis induced by administration of LPS.

These experiments were performed based on information reported by Rivier et al., *Endocrinology* 125:2800–2805 (1989), which is incorporated herein by reference. Adult female Balb/c mice were provided food and water ad libitum. Mice were injected ip every four hours for 40 hr with 30 to 300 µg EX-2 in 0.2 ml saline (treated group) or with 0.2 ml saline, alone (control group) (10 mice per group). Immediately following the first injection, 0.6 mg LPS endotoxin in 0.2 ml saline was administered to each mouse. Following LPS injection, EX-2 or saline was administered to the treated mice or the control mice, respectively, every 4 hr for 36 hr. As shown in Table I, mice that received a total of 3.3 mg EX-2 (11 injections of 300 µg each) had an 83% increase in survival as compared to control mice.

EXAMPLE VII

Reduction in Interleukin-1β-Induced Hyperalgesia

This example describes the effectiveness of a cytokine restraining agent, EX-2, in providing pain prophylaxis.

These experiments were performed using a modification of the methods described by Poole et al., *Br. J. Pharmacol.* 106:489–492 (1992); Foilenfant et al., *Br. J. Pharmacol.* 98:41–43 (1989); and Randall and Sellito, *Arch. Internatl. Pharmacodyn.* 111:409–419 (1957), each of which is incorporated herein by reference. Adult male Sprague-Dawley rats (175-275 g) were tested for hyperalgesia by a paw pressure technique using variable pressure instrumentation (IITC Life Sciences; Woodland Hills, Calif.). Rats were acclimated to the housing environment and were handled for three days prior to beginning a training session. On the day before the hyperalgesia experiments was to begin, each rat was placed into a sock and two variable paw pressure tests were performed 15 min apart. The next day, the rats were pretested to determine the pressure (mm Hg) at which each animal exhibited escape reflexes such as whole body struggling and/or vocalization. Approximately 5-10% of the rats were non-responders and were eliminated from further experiments.

Animals that responded to the paw pressure were pretreated by ip injection of various concentrations of EX-2 in a volume of 1 ml/kg (treated) or saline, alone (control). After twenty minutes, 100 μl of IL-1β (1U/100 μl) was administered to rats via intraplantar injection. Two hr after IL-1 administration, rats were subjected to two additional paw pressure tests and the increase in mm Hg of pressure that could be applied to the EX-2-treated rats as compared to the control rats was determined. As shown in Table I, treatment with 1 μg EX-2 increased the amount of pressure the rats would tolerate by 125% as compared to the control rats.

EXAMPLE VIII

Adult Respiratory Distress Syndrome

This example describes the effectiveness of a cytokine restraining agent, EX-2, in minimizing respiratory distress syndrome in LPS-treated rats.

These experiments were performed using a modification of the methods described by Ulich et al., Am. J. Pathol. 141:61-68 (1992) and by Wheelden et al., Lab. Animals 26:29-37 (1992), each of which is incorporated herein by reference. Male Harlan Sprague-Dawley rats were anesthetized using a mixture of 70 mg/kg ketamine and 6 mg/kg rompun injected ip. A 2-3 cm incision was made in the neck of each anesthetized rat and its trachea was exposed by blunt dissection of the surrounding soft tissue. The rats were suspended on a near vertical slab and intratracheal injections were performed by inserting into the exposed trachea, at a point 1 cm posterior to the larynx, a 25 G×½ inch needle attached to a 1 cc syringe.

Each rat received 0.5 ml/kg of saline or 0.5 ml/kg of 10 mg/ml (5 mg/kg) LPS endotoxin via slow intratracheal administration. Immediately following administration of the LPS endotoxin, rats were injected ip with 1 ml/kg of either saline (control) or saline containing various concentrations of EX-2 (treated). The rats were maintained in the elevated position for 1-2 min to facilitate distribution of the LPS and saline into the lung. The incisions were closed and the rats were allowed to recover. Two and four hr post-intratracheal injection, saline or EX-2 again was administered ip to control and treated rats, respectively.

At 6 hr post-intratracheal injection, the rats were re-anesthetized and exsanguinated via cardiac puncture. Serum was collected and saved. The neck and chest were opened to expose the trachea and lungs, the lungs were lavaged with 6×5 ml saline using a 27 G×¾ inch needle and the lavage fluid was pooled.

The total polymorphonuclear leukocytes (PMN; neutrophils) in the broncho-alveolar lavage fluid were counted in the EX-2-treated rats and compared with the number in the control rats. As shown in Table I, treatment with 100 μg/kg EX-2 inhibited the increase in PMN infiltration in LPS-treated lungs by 58%.

EXAMPLE IX

Inhibition of Interleukin-1β- or Lipopolysaccharide-Induced Temperature Increase This example describes the effectiveness of a cytokine restraining agent, EX-2, at inhibiting body temperature increase in rats in response to two different agents.

Male Wistar rats (45-75 days old) were placed in a temperature controlled room held at 26° C., which is thermoneutral for the normal body temperature of rats, and were maintained in the room with free access to food and water for 24 hr prior to testing. On the morning of the study, rats were marked for identification and weighed. The temperature of each rat was determined by placing the animal in a restraining cage designed to minimize stress and inserting a temperature probe (YSI probe #402) 3-5 cm into the animal's rectum. The temperature was recorded 15 sec after the reading stabilized. Measurements were repeated 1 hr later to establish a baseline temperature for each rat.

After the baseline temperatures were established, rats were injected ip with saline, IL-1β or LPS endotoxin. Rats then were injected ip with either saline (control) or various concentrations of EX-2 (treated). The temperature of the rats was measured every hour for 6 hr and the inhibition by EX-2 of the rise in temperature due to IL-1β or LPS was determined. As shown in Table I, treatment with 500 μg/kg EX-2 inhibited IL-1-induced fever by 52% and treatment with 50 μg/kg EX-2 inhibited LPS-induced fever by 45% when measured 6 hr following LPS injection.

Although the invention has been described with reference to the examples provided above, it should be understood that various modifications can be made without departing from the spirit of the invention. Accordingly, the invention is limited only by the following claims.

We claim:

1. A cytokine restraining peptide, having:

$X_1 - X_2 - $ His $-$ (D) Phe $-$ Arg $-$ (D) Trp $- X_3$, wherein:

$X_1$ is

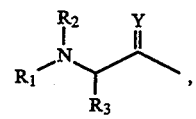

H or COCH$_3$;

$X_2$ is

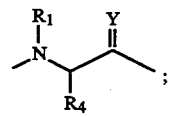

and $X_3$ is

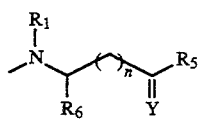

or NH$_2$;

wherein Y is O, H$_2$ or S;

R$_1$ is H, COCH$_3$, C$_2$H$_5$, CH$_2$Ph, COPh, COOCH$_2$Ph, COO-t-butyl, CH$_2$CO-(polyethylene glycol) or A;

R$_2$ is H or COCH$_3$;

R$_3$ is a linear or branched alkyl group having 1 to 6 carbon atoms;

R$_4$ is (CH$_2$)$_m$-CONH$_2$, (CH$_2$)$_m$-CONHR$_1$ or (CH$_2$)$_m$-CONHA;

R$_5$ is OH, OR$_3$, NH$_2$, SH, NHCH$_3$, NHCH$_2$Ph or A; and

R$_6$ is H or R$_3$;

and wherein "Ph" is C$_6$H$_5$, "m" is 1, 2 or 3, "n" is 0, 1, 2 or 3, and "A" is a carbohydrate having the general formula:

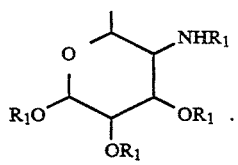

2. A cytokine restraining peptide, having:

X$_4$ - His - (D)Phe - Arg - (D)Trp - X$_3$, wherein:
X$_4$ is

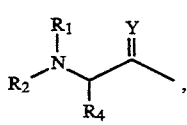

H or COCH$_3$; and
X$_3$ is

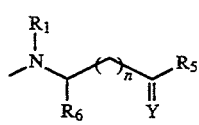

or NH$_2$;

wherein Y is O, H$_2$ or S;

R$_1$ is H, COCH$_3$, C$_2$H$_5$, CH$_2$Ph, COPh, COOCH$_2$Ph, COO-t-butyl, CH$_2$CO-(polyethylene glycol) or A;

R$_2$ is H or COCH$_3$;

R$_4$ is (CH$_2$)$_m$-CONH$_2$, (CH$_2$)$_m$-CONHR$_1$ or (CH$_2$)$_m$-CONHA;

R$_5$ is OH, OR$_3$, NH$_2$, SH, NHCH$_3$, NHCH$_2$Ph or A; and

R$_6$ is H or R$_3$;

and wherein "Ph" is C$_6$H$_5$, "m" is 1, 2 or 3, "n" is 0, 1, 2 or 3, and "A" is a carbohydrate having the general formula:

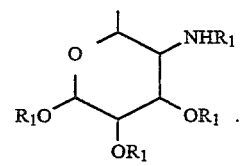

3. The peptide of claim 1 or 2, wherein the amino terminus is modified.

4. The peptide of claim 3, wherein said modification is acetylation.

5. The peptide of claim 1 or 2, wherein the carboxy terminus is modified.

6. The peptide of claim 5, wherein said modification is amidation.

7. The peptide of claim 1 or 2, wherein R$_1$ is selected from the group consisting of C$_2$H$_5$ and CH$_2$Ph and wherein R$_2$ is selected from the group consisting of H and COCH$_3$.

8. The peptide of claim 1 or 2, wherein R$_1$ and R$_2$ are the same moiety, said moiety selected from the group consisting of H, C$_2$H$_5$ and CH$_2$Ph.

9. The peptide of claim 1, wherein X$_1$ is selected from the group consisting of norleucine, norvaline, leucine and isoleucine.

10. The peptide of claim 1, wherein R$_5$ is covalently bound to X$_1$, said covalent bond forming a cyclic peptide.

11. A cytokine restraining peptide, having Nle -Gln - His - (D) Phe - Arg - (D) Trp - Gly-NH$_2$.

12. The peptide of claim 11, wherein the amino terminus of said peptide is acetylated.

13. The peptide of claim 2, wherein R$_5$ is covalently bound to X$_4$, said covalent bond forming a cyclic peptide.

14. A composition of matter comprising a cytokine restraining peptide and a pharmaceutically acceptable carrier, said peptide having:

X$_1$ - X$_2$ - His - (D)Phe - Arg - (D)Trp - X$_3$, wherein:
X$_1$ is

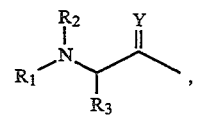

H or COCH$_3$;
X$_2$ is

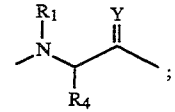

and X$_3$ is

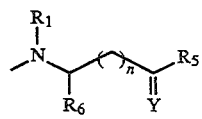

or NH$_2$;

wherein Y is O, H$_2$ or S;

$R_1$ is H, $COCH_3$, $C_2H_5$, $CH_2Ph$, $COPh$, $COO$-t-butyl, $COOCH_2Ph$, $CH_2CO$-(polyethylene glycol), A or $R_2$;

$R_2$ is H or $COCH_3$;

$R_3$ is a linear or branched alkyl group having 1 to 6 carbon atoms;

$R_4$ is $(CH_2)_m$-$CONH_2$, $(CH_2)_m$-$CONHR_1$ or $(CH_2)_m$-$CONHA$;

$R_5$ is OH, $OR_3$, $NH_2$, SH, $NHCH_3$, $NHCH_2Ph$ or A;

$R_6$ is H or $R_3$;

and wherein "Ph" is $C_6H_5$, "m" is 1, 2 or 3, "n" is 0, 1, 2 or 3, and "A" is a carbohydrate having the general formula:

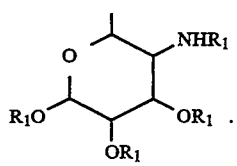

15. A composition of matter comprising a cytokine restraining peptide and a pharmaceutically acceptable carrier, said peptide having:

$X_4$ - His - (D)Phe - Arg - (D)Trp - $X_3$, wherein:

$X_4$ is

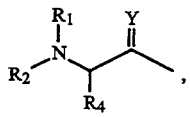

H or $COCH_3$; and $X_3$ is

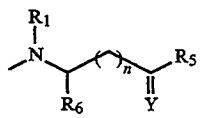

or $NH_2$;

wherein Y is O, $H_2$ or S;

$R_1$ is H, $COCH_3$, $C_2H_5$, $CH_2Ph$, $COPh$, $COO$-t-butyl, $COOCH_2Ph$, $CH_2CO$-(polyethylene glycol), A or $R_2$;

$R_2$ is H or $COCH_3$;

$R_4$ is $(CH_2)_m$-$CONH_2$, $(CH_2)_m$-$CONHR_1$ or $(CH_2)_m$-$CONHA$;

$R_5$ is OH, $OR_3$, $NH_2$, SH, $NHCH_3$, $NHCH_2Ph$ or A;

$R_6$ is H or $R_3$;

and wherein "Ph" is $C_6H_5$, "m" is 1, 2 or 3, "n" is 0, 1, 2 or 3, and "A" is a carbohydrate having the general formula:

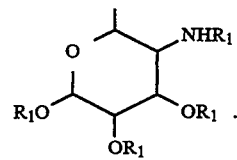

16. A method of restraining pathologically elevated cytokine activity in a subject, comprising administering to the subject an effective amount of the pharmaceutical composition of claim 14 or 15.

17. The method of claim 16, wherein said pathologically elevated cytokine activity is due to inflammation.

18. The method of claim 16, wherein said pathologically elevated cytokine activity is due to cachexia.

19. The method of claim 16, wherein said pathologically elevated cytokine activity is due to a pathoimmunogenic disease.

20. The method of claim 16, wherein said composition is administered more than one time.

21. The method of claim 16, wherein said composition is administered topically.

22. The method of claim 16, wherein said composition is administered parenterally.

23. The method of claim 16, wherein said composition is administered via intubation.

24. The method of claim 16, wherein said composition is administered via transdermal iontophoresis.

* * * * *